United States Patent
Kasamatsu et al.

(10) Patent No.: US 10,806,347 B2
(45) Date of Patent: Oct. 20, 2020

(54) PHOTOACOUSTIC MEASUREMENT APPARATUS AND PROBE FOR PHOTOACOUSTIC MEASUREMENT

(71) Applicant: FUJIFILM Corporation, Tokyo (JP)

(72) Inventors: Tadashi Kasamatsu, Ashigarakami-gun (JP); Kazuhiro Hirota, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 394 days.

(21) Appl. No.: 15/388,578

(22) Filed: Dec. 22, 2016

(65) Prior Publication Data

US 2017/0100041 A1 Apr. 13, 2017

Related U.S. Application Data

(63) Continuation of application No. PCT/JP2015/002928, filed on Jun. 11, 2015.

(30) Foreign Application Priority Data

Jun. 26, 2014 (JP) ................. 2014-131053

(51) Int. Cl.
*A61B 5/00* (2006.01)
*G01N 29/06* (2006.01)
(Continued)

(52) U.S. Cl.
CPC .............. *A61B 5/0095* (2013.01); *A61B 5/72* (2013.01); *A61B 5/742* (2013.01);
(Continued)

(58) Field of Classification Search
CPC .... A61B 5/0095; A61B 5/72; G01N 29/2418; G01N 29/226
See application file for complete search history.

(56) References Cited

U.S. PATENT DOCUMENTS

2005/0187471 A1* 8/2005 Kanayama ........... A61B 5/0091
600/437
2007/0090271 A1 4/2007 Kobayashi
(Continued)

FOREIGN PATENT DOCUMENTS

JP 2007-111338 A 5/2007
JP 2010-264044 A 11/2010
(Continued)

OTHER PUBLICATIONS

Japanese Office Action issued in Japanese Application No. 2016-529025 dated Jul. 4, 2017, together with an English translation.
(Continued)

*Primary Examiner* — Bill Thomson
*Assistant Examiner* — Aminah Asghar
(74) *Attorney, Agent, or Firm* — Birch, Stewart, Kolasch & Birch, LLP

(57) ABSTRACT

A probe has a light guide unit that guides the measurement light, an acoustic wave detection unit that detects a photoacoustic wave, and a storage unit that stores light intensity profile information that represents the light intensity profile of the measurement light emitted by the probe, and transmits a signal of the photoacoustic wave detected by the acoustic wave detection unit to the signal processing unit in a state in which the probe is mounted in the apparatus body. The apparatus body has a reading unit that reads the light intensity profile information from the storage unit, and the intensity adjusting unit adjusts the intensity of the measurement light employing the light intensity profile information read by the reading unit.

9 Claims, 7 Drawing Sheets

(51) Int. Cl.
G01N 29/22 (2006.01)
G01N 29/24 (2006.01)
(52) U.S. Cl.
CPC ....... *G01N 29/0654* (2013.01); *G01N 29/226* (2013.01); *G01N 29/2418* (2013.01); *G01N 2291/02483* (2013.01)

(56) References Cited

U.S. PATENT DOCUMENTS

| 2011/0270071 A1 | 11/2011 | Furukawa |
| 2012/0325006 A1 | 12/2012 | Suzuki |
| 2013/0281819 A1 | 10/2013 | Schmid |

FOREIGN PATENT DOCUMENTS

| JP | 2011-229660 A | 11/2011 |
| JP | 2011-229735 A | 11/2011 |
| JP | 2012-061226 A | 3/2012 |
| JP | 2013-027482 A | 2/2013 |
| JP | 2013-099566 A | 5/2013 |
| WO | WO 2013/188707 A1 | 12/2013 |

OTHER PUBLICATIONS

International Search Report (PCT/ISA/210) issued in PCT/JP2015/002928, dated Oct. 20, 2015.
Written Opinion (PCT/ISA/237) issued in PCT/JP2015/002928, dated Oct. 20, 2015.
Japanese Office Action, dated Nov. 14, 2017, for corresponding Japanese Application No. 2016-529025, with an English translation.

* cited by examiner

PHOTOACOUSTIC MEASUREMENT APPARATUS AND PROBE FOR PHOTOACOUSTIC MEASUREMENT

CROSS REFERENCE TO RELATED APPLICATIONS

The present application is a Continuation of PCT International Application No. PCT/JP2015/002928 filed on Jun. 11, 2015, which claims priority under 35 U.S.C. § 119 (a) to Japanese Patent Application No. 2014-131053 filed on Jun. 26, 2014. Each of the above applications is hereby expressly incorporated by reference, in its entirety, into the present application.

BACKGROUND OF THE INVENTION

1. Field of the Invention

The present invention relates to a photoacoustic measurement apparatus for measuring a photoacoustic wave generated within a subject and a probe for photoacoustic measurement provided in the apparatus.

2. Description of the Related Art

As a kind of image examination method capable of examining the state of the inside of a subject (for example, a body) in a non-invasive manner, ultrasonography is known. In ultrasound examination, an ultrasound probe capable of transmitting and receiving ultrasound waves is used. When ultrasound waves are transmitted to a subject from the ultrasound probe, the ultrasound waves propagate through the subject to be reflected on tissue interfaces. By receiving the reflected ultrasound waves using the ultrasound probe and calculating the distance based on the time until the reflected ultrasound waves return to the ultrasound probe, it is possible to image the state of the inside.

In addition, photoacoustic imaging for imaging the inside of a subject using the photoacoustic effect is known. In general, in photoacoustic imaging, for example, pulsed laser light is emitted into the subject. In the subject, tissue absorbs the energy of the pulsed laser light, and ultrasound waves (photoacoustic waves) due to adiabatic expansion due to the energy are generated. By detecting the photoacoustic waves using an ultrasound probe or the like and forming a photoacoustic image based on the detection signal, it is possible to visualize the inside of the subject based on the photoacoustic waves.

In such measurement of acoustic waves, various probes having different shapes, structures, and performance depending on the measurement conditions, such as a measurement purpose, a measurement method, and a measurement part, are available. For example, a linear type probe in which transducers are linearly arranged is used in the case of measuring the abdomen from the outside of the body, and a convex type probe in which transducers are arranged in an arc shape is used in the case of measuring the rectum to the prostate. In addition, a probe in which the center frequency of a detection band is high (for example, 20 MHz) is used in a case where high-resolution measurement or a high-quality image is required, and a probe in which the center frequency is low (for example, 10 MHz) is used in a case where such high accuracy is not required.

In general, in clinical practice, a plurality of different types of probe are available for one ultrasound device, and desired measurement is performed by switching a probe or selecting a probe to be used from probes already mounted depending on the measurement conditions.

Incidentally, in photoacoustic imaging, in the case of using a laser as a light source, the maximum value of the light density (amount of light per unit area) emitted to the body should not exceed the maximum permissible exposure (MPE) defined by the standards of laser safety standards. Therefore, JP2011-229735A discloses measuring the light density distribution of light emitted to the body and adjusting the amount of light such that the maximum value does not exceed the maximum permissible exposure.

SUMMARY OF THE INVENTION

However, in order to measure the light density as in JP2011-229735A, measurement means therefor is required. Accordingly, the apparatus becomes complicated, and the cost for manufacturing the apparatus is increased. In addition, in the case of using a handheld type probe (probe having a grip portion for a user to grip), it is difficult to measure the light density accurately since the position of the probe is not fixed. In addition, in the case of using a plurality of probes depending on the measurement conditions as described above, it is necessary to measure the light density at every installation or switching of a probe, which is troublesome work.

The present invention has been made in view of the aforementioned problems, and it is an object of the present invention to provide a probe for photoacoustic measurement and a photoacoustic measurement apparatus capable of easily setting the light density of measurement light within an appropriate range in the case of using a probe for photoacoustic measurement that is detachable and attachable from and to the apparatus body.

In order to solve the aforementioned problems, a photoacoustic measurement apparatus of the present invention comprises: an apparatus body having a signal processing unit that performs signal processing on a photoacoustic wave; a probe that is detachable and attachable from and to the apparatus body and that emits measurement light incident on the probe toward a subject; and an intensity adjusting unit that adjusts an intensity of the measurement light. The probe has a light guide unit that guides the measurement light, an acoustic wave detection unit that detects the photoacoustic wave generated within the subject according to emission of the measurement light from the light guide unit, and a storage unit that stores information relevant to setting of the intensity of the measurement light, and transmits a signal of the photoacoustic wave detected by the acoustic wave detection unit to the signal processing unit in a state in which the probe is mounted in the apparatus body. The apparatus body has a reading unit that reads the information from the storage unit, and the intensity adjusting unit adjusts the intensity of the measurement light before the measurement light is incident on the probe based on the information read by the reading unit.

In this specification, the "information relevant to the setting of the intensity of the measurement light" refers to information that is useful in setting the intensity of the measurement light before the measurement light is incident on the probe to an intensity suitable for the measurement method or purpose.

In the photoacoustic measurement apparatus of the present invention, it is preferable that the information includes identification information for identifying a type of the probe. It is preferable that the identification information includes type information for identifying that the type of the probe is any one of a linear type, a convex type, and a sector type. In addition, it is preferable that the identification information includes emission area information indicating an area of a light emitting surface of the probe.

In the photoacoustic measurement apparatus of the present invention, it is preferable that the information includes optical performance information indicating optical performance of the probe. It is preferable that the optical performance information includes light density information indicating a degree of change in a light density when the measurement light is emitted from the probe with respect to a light density when the measurement light is incident on the probe. The optical performance information can include transmittance information indicating a transmittance of the measurement light within the probe, or can include light intensity profile information indicating a light intensity profile when the measurement light is emitted from the probe.

In the photoacoustic measurement apparatus of the present invention, it is preferable that the intensity adjusting unit acquires adjustment conditions, which are associated with the information by a look-up table, with reference to the look-up table, and adjusts the intensity of the measurement light according to the adjustment conditions.

Alternatively, in the photoacoustic measurement apparatus of the present invention, it is preferable that the intensity adjusting unit adjusts the light intensity by setting a calculated value, which is calculated based on the information, to a target value of the intensity of the measurement light.

In the photoacoustic measurement apparatus of the present invention, it is preferable that the information is target value information indicating a target value of the intensity of the measurement light and the intensity adjusting unit adjusts the light intensity by setting a numerical value indicated by the target value information to the target value of the intensity of the measurement light.

In the photoacoustic measurement apparatus of the present invention, it is preferable that the intensity adjusting unit increases or decreases an amount of attenuation of the intensity of the measurement light using a variable attenuator. In this case, it is preferable that the variable attenuator is a polarization variable attenuator.

In the photoacoustic measurement apparatus of the present invention, it is preferable that the intensity adjusting unit increases or decreases a beam diameter of the measurement light when the measurement light is incident on the light guide unit.

In the photoacoustic measurement apparatus of the present invention, it is possible to adopt a configuration in which the information is attenuation necessity information indicating whether or not it is necessary to attenuate the intensity of the measurement light and the intensity adjusting unit adjusts the intensity of the measurement light by controlling presence of an attenuator according to the attenuation necessity information.

In the photoacoustic measurement apparatus of the present invention, it is preferable that, in a case where there is a plurality of probes mounted in the apparatus body, the reading unit reads the information from the storage unit of a probe designated by a user.

In the photoacoustic measurement apparatus of the present invention, it is preferable that the probe is a handheld type probe.

A probe for photoacoustic measurement of the present invention is a probe that is detachable and attachable from and to an apparatus body having a signal processing unit for performing signal processing on a photoacoustic wave and that guides measurement light up to a subject. The probe for photoacoustic measurement comprises: a light guide unit that guides the measurement light; an acoustic wave detection unit that detects the photoacoustic wave generated within the subject according to emission of the measurement light from the light guide unit; and a storage unit that stores information relevant to setting of the intensity of the measurement light. The probe for photoacoustic measurement transmits a signal of the photoacoustic wave detected by the acoustic wave detection unit to the signal processing unit in a state in which the probe is mounted in the apparatus body.

By the photoacoustic measurement apparatus and the probe for photoacoustic measurement of the present invention, it is possible to easily set the light density of measurement light in the case of using a probe for photoacoustic measurement that is detachable and attachable from and to the apparatus body.

Figure 2:
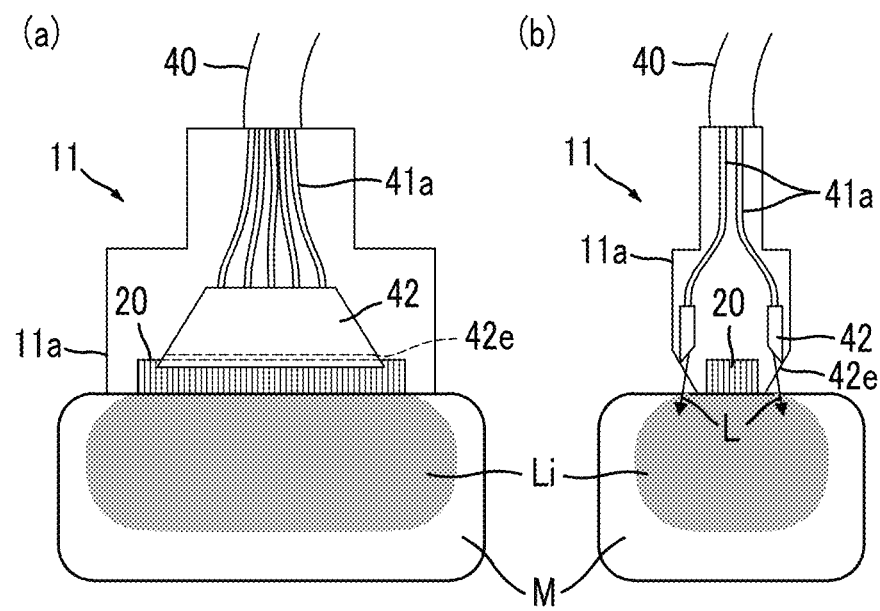

(a) of FIG. 2 is a front cross-sectional view schematically showing the configuration of a probe according to the first embodiment, and (b) of FIG. 2 is a side cross-sectional view schematically showing the configuration of the probe according to the first embodiment.

Figure 3A:
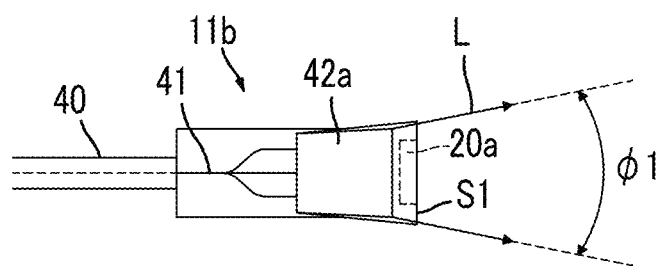
Figure 3B:
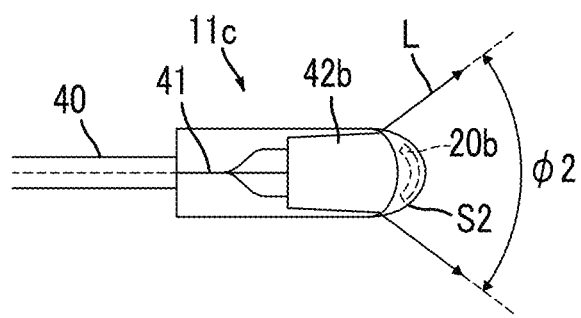

FIG. 3A is a schematic cross-sectional view showing a linear type probe, and FIG. 3B is a schematic cross-sectional view showing a convex type probe.

Figure 4A:
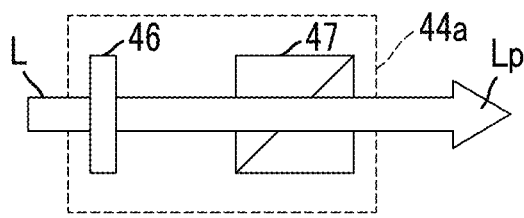
Figure 4B:
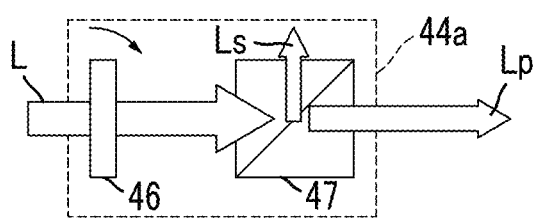
Figure 4C:
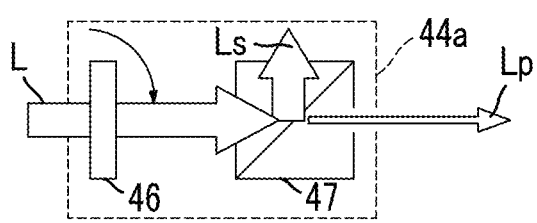

FIGS. 4A to 4C are schematic diagrams showing an example of a variable attenuator.

Figure 5A:
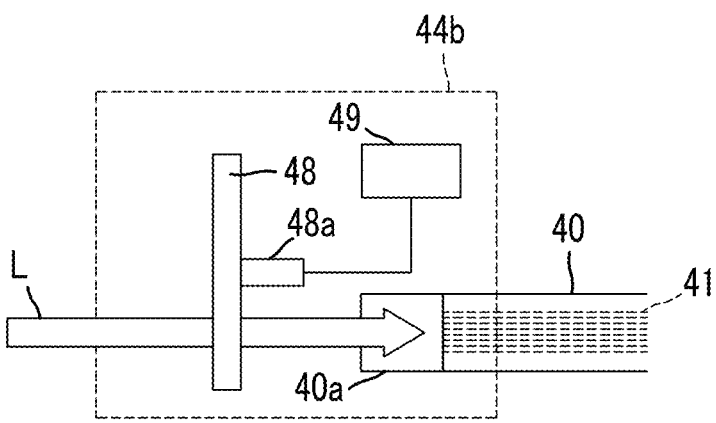
Figure 5B:
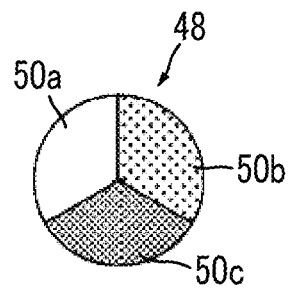

FIGS. 5A and 5B are schematic diagrams showing another example of the variable attenuator.

Figure 6:
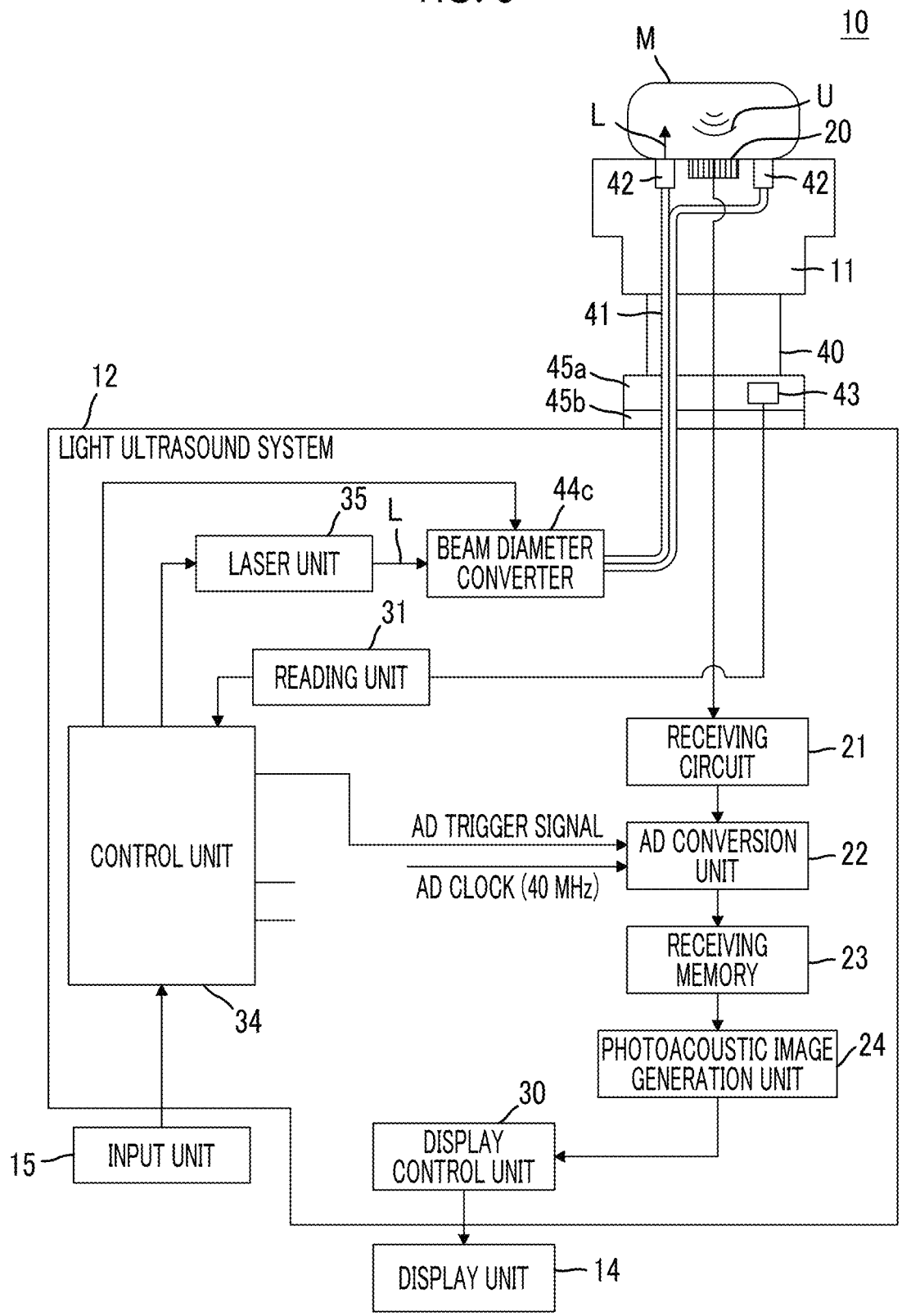

FIG. 6 is a block diagram schematically showing the configuration of a photoacoustic image generation apparatus according to a second embodiment.

Figure 7A:
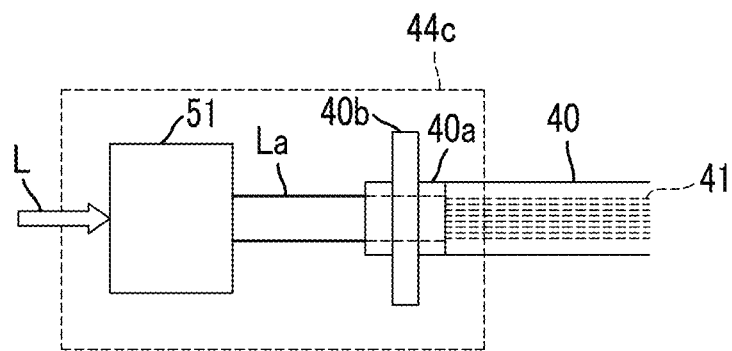
Figure 7B:
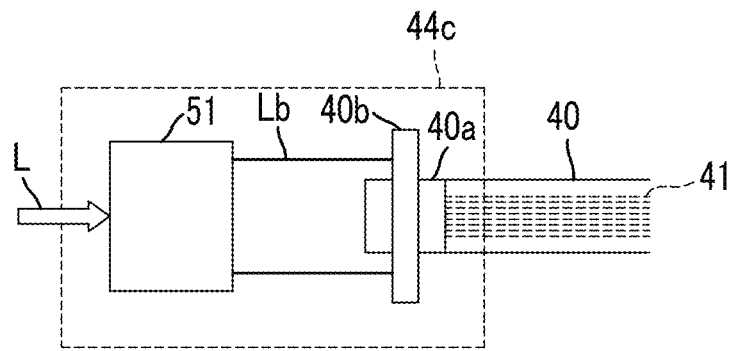

FIGS. 7A and 7B are schematic diagrams showing an example of a beam diameter converter.

Figure 8:
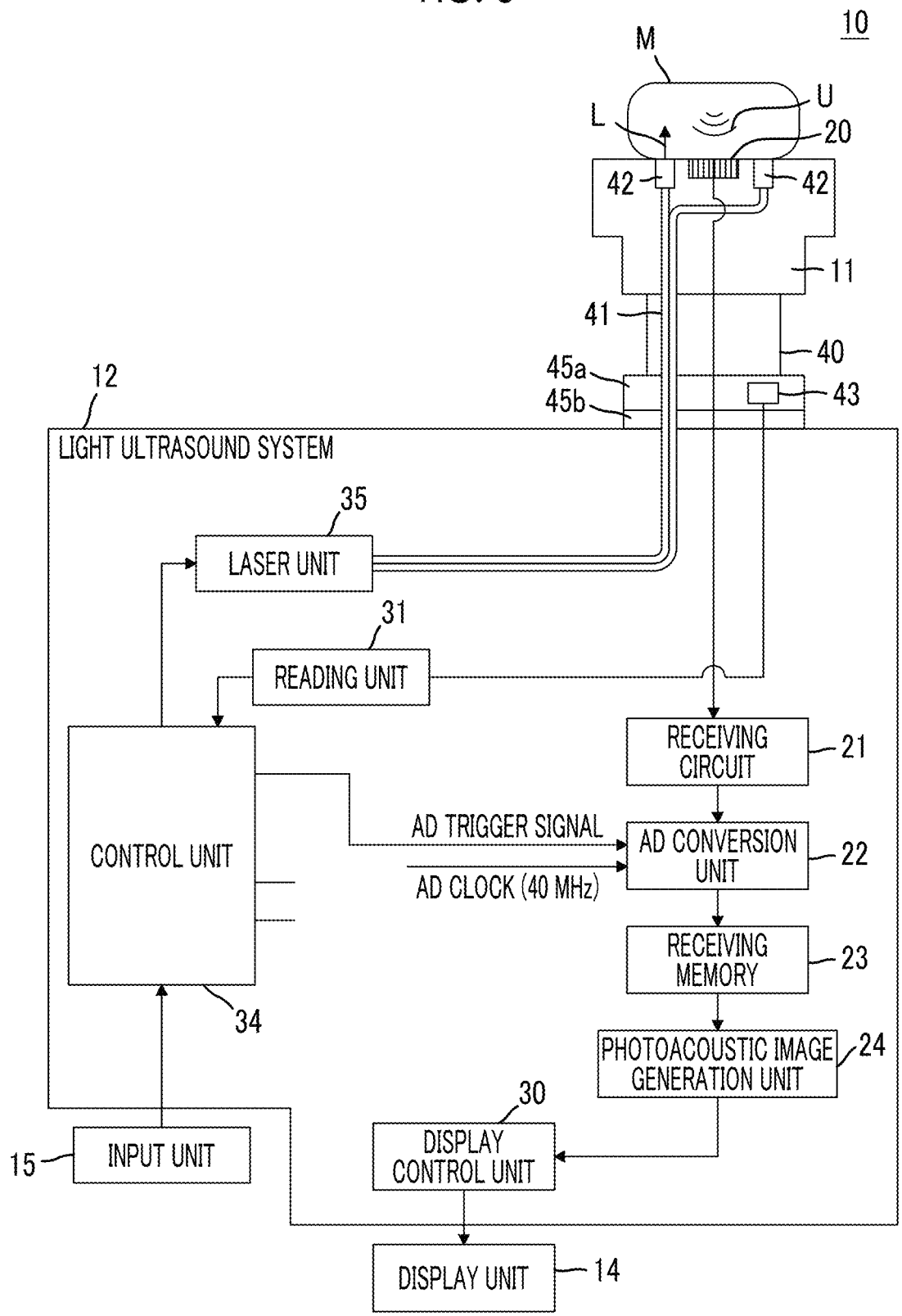

FIG. 8 is a block diagram schematically showing the configuration of a photoacoustic image generation apparatus according to a third embodiment.

Figure 9:
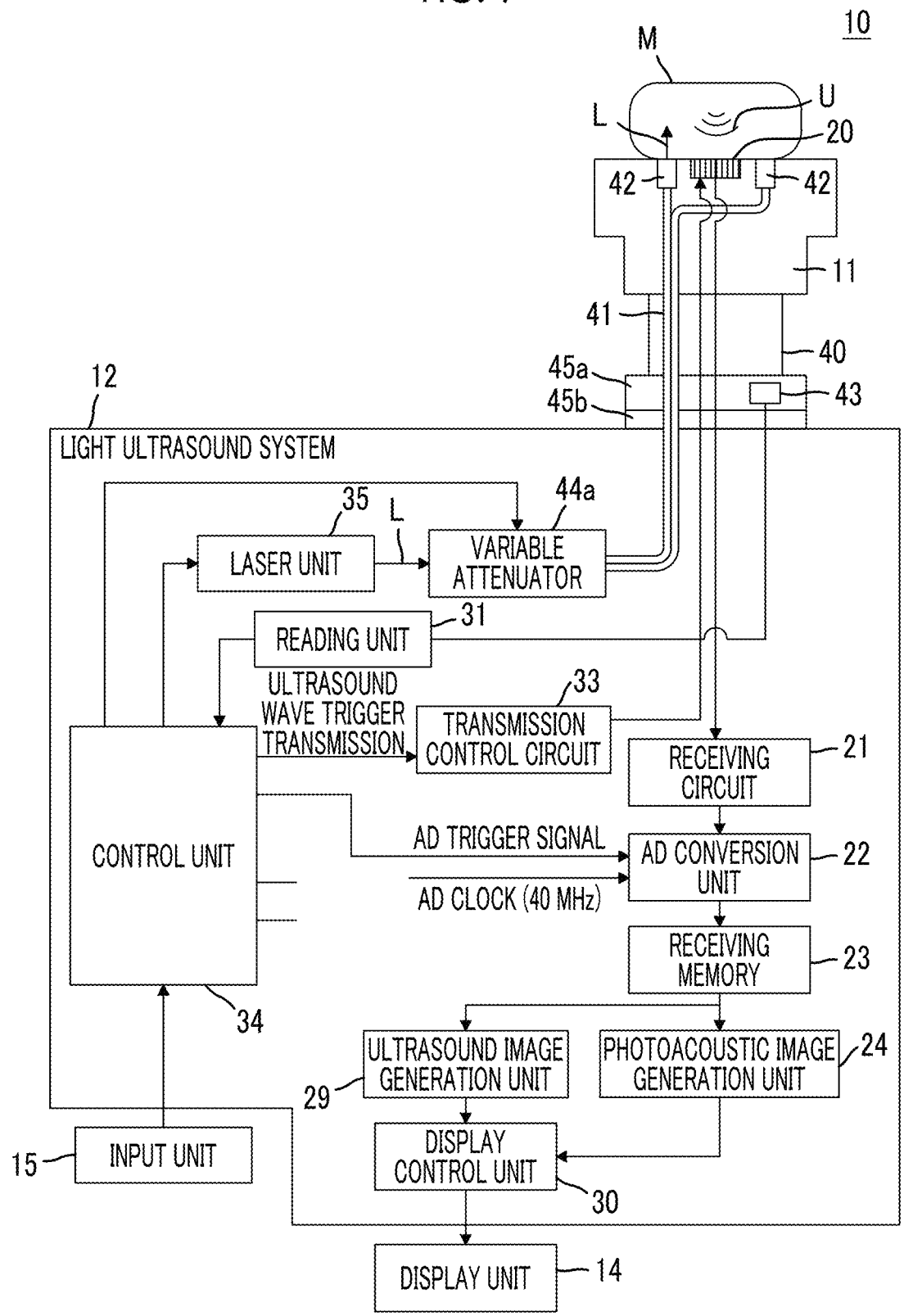

FIG. 9 is a block diagram schematically showing the configuration of a photoacoustic image generation apparatus according to a fourth embodiment.

DESCRIPTION OF THE PREFERRED EMBODIMENTS

Hereinafter, embodiments of the present invention will be described with reference to the accompanying diagrams. However, the present invention is not limited to these. In addition, the scale of each component is appropriately adjusted in order to have a recognizable size in the diagrams described below.

First Embodiment

Figure 1:
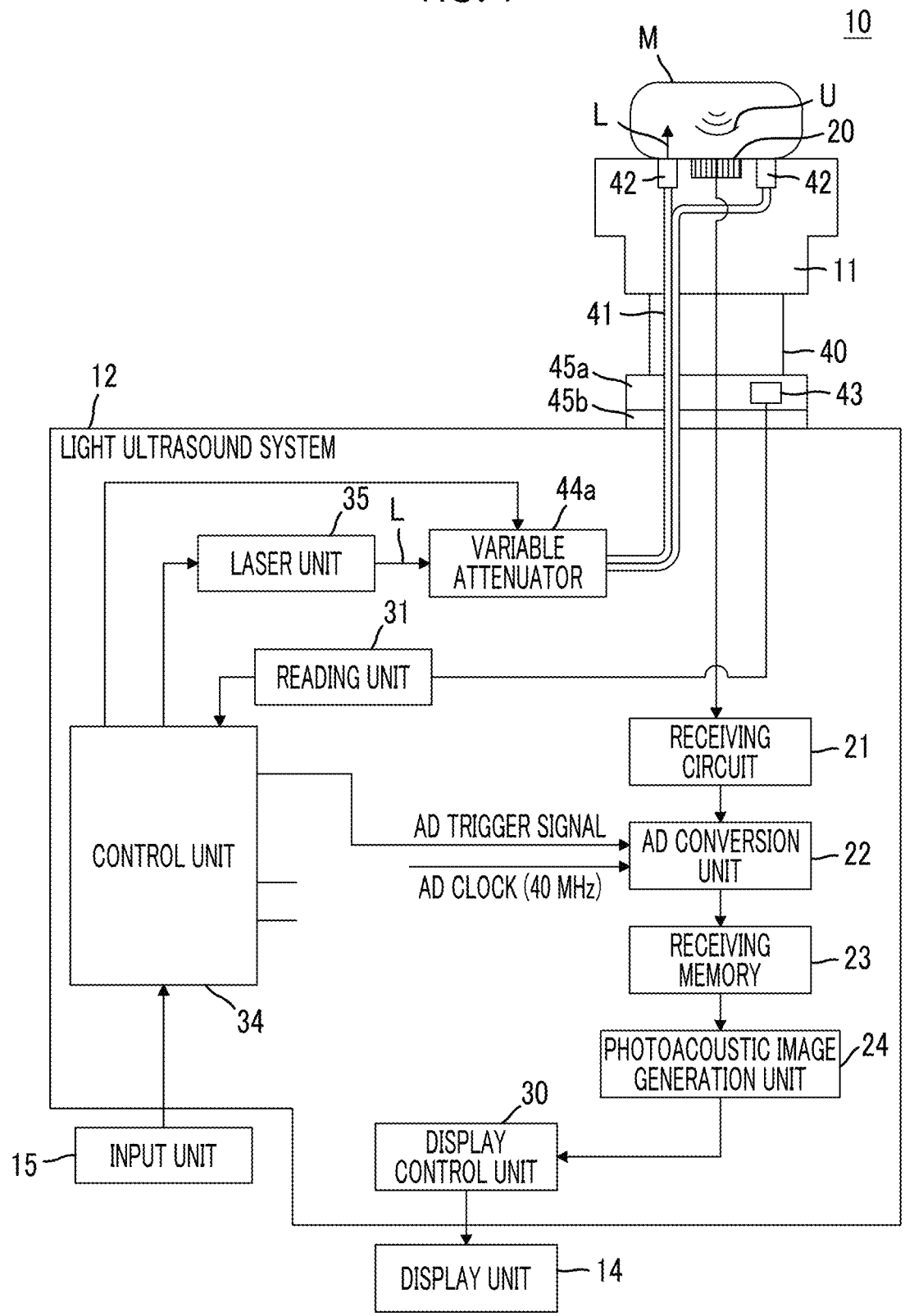
FIG. 1 is a block diagram schematically showing the configuration of a photoacoustic image generation apparatus (photoacoustic measurement apparatus) according to a first embodiment.

A photoacoustic measurement apparatus according to a first embodiment will be described. In the present embodiment, the photoacoustic measurement apparatus is, for example, a photoacoustic image generation apparatus 10 that detects photoacoustic waves with a probe and generates a photoacoustic image based on the signal of the detected photoacoustic wave. FIG. 1 is a block diagram schematically showing the configuration of a photoacoustic image generation apparatus (photoacoustic measurement apparatus) according to the present embodiment. (a) of FIG. 2 is a front cross-sectional view schematically showing the configuration of a probe according to the present embodiment, and (b) of FIG. 2 is a side cross-sectional view schematically showing the configuration of the probe according to the present embodiment.

As shown in FIG. 1, the photoacoustic image generation apparatus 10 includes a probe 11, a light ultrasound system 12, a display unit 14, and an input unit 15. In the embodiment of the present invention, an ultrasound wave is used as an acoustic wave. However, the present invention is not limited to the ultrasound wave, and an acoustic wave having an audible frequency may be used if an appropriate frequency can be selected according to an examination target, measurement conditions, or the like.

<Probe>

As shown in FIG. 1 and (a) and (b) of FIG. 2, for example, the probe 11 includes a transducer array 20, a cable 40, a bundle fiber 41 included in the cable 40, two light emitting units 42 disposed so as to interpose the transducer array 20 therebetween, a storage unit 43, a connector unit 45a provided at one end of the cable 40, and a housing 11a. The housing 11a contains the transducer array 20, a portion of the bundle fiber 41 on the emission end side, and the two light emitting units 42. The bundle fiber 41 and the two light emitting units 42 correspond to a light guide unit of the present invention as a whole.

The probe 11 emits ultrasound waves toward a subject, or detects acoustic waves U propagating through a subject M. That is, the probe 11 can perform emission (transmission) of ultrasound waves to the subject M and detection (reception) of reflected ultrasound waves (reflected acoustic waves) that return due to reflection from the subject M. In addition, the probe 11 can also detect photoacoustic waves generated in the subject M due to absorption of laser light by an absorber in the subject M. As the absorber, for example, blood vessels, a metal member, and the like can be mentioned. In addition, although the photoacoustic wave is also an ultrasound wave, it is assumed hereinafter, for the sake of convenience, that the "ultrasound wave" means an acoustic wave transmitted by the probe and its reflected wave and that the "photoacoustic wave" means an acoustic wave generated in the subject M by the photoacoustic effect due to the emission of measurement light.

The transducer array 20 is configured to include a plurality of ultrasound transducers (or acoustic wave detection elements) arranged in a one-dimensional or two-dimensional manner, for example. In the present embodiment, the transducer array 20 or each of the ultrasound transducers corresponds to an acoustic wave detection unit of the present invention. For example, the ultrasound transducer is a piezoelectric element formed of a polymer film, such as piezoelectric ceramics or polyvinylidene fluoride (PVDF). The ultrasound transducer has a function of converting the received signal into an electrical signal in a case where the acoustic waves U is received, and the electrical signal generated by the ultrasound transducer is output to a receiving circuit 21 to be described later. The shape of the transducer array 20 is selected according to an imaging part from the types, such as a sector type, a linear type, and a convex type.

The bundle fiber 41 is formed by bundling a plurality of optical fibers 41a, and guides laser light L from a laser unit 35 to the light emitting unit 42. The bundle fiber 41 is not particularly limited, and known fibers, such as a quartz fiber, can be used. The bundle fiber 41 is branched for each optical fiber 41a on the emission side, and is connected to the light emitting unit 42.

The light emitting unit 42 is a unit that emits the laser light guided by the bundle fiber 41 to the subject M. As shown in FIG. 1 and (a) and (b) of FIG. 2, in the present embodiment, the two light emitting units 42 are disposed on both sides of the transducer array 20 in the elevation direction (direction that is perpendicular to the array direction of the transducer array and is parallel to the detection plane) so as to face each other with the transducer array 20 interposed therebetween. In (b) of FIG. 2, the light emitting units 42 are disposed so as to be spaced upward from the tangential plane including the detection plane of the transducer array 20 (on the transducer array side with respect to the tangential plane). Therefore, it is possible to ensure the propagation distance of the measurement light emitted from the light emitting unit. In addition, a part of the emission end surface (for example, the corner of the emission end surface) may be in contact with the tangential plane.

An emission end surface 42e crossing the internal optical axis of the light emitting unit 42 is formed at the emission end of the light emitting unit 42, and measurement light is refracted when exiting the emission end surface 42e. At this time, the refractive index of the inside of the light emitting unit 42 is larger than the refractive index in the air. Accordingly, measurement light L is emitted from the light emitting unit 42 in a state in which the optical axis on the emission end surface is inclined to the opposite side of a side on which the transducer array 20 is present with respect to the normal direction of the detection plane of the transducer array 20 (acoustic wave detection unit) (refer to (b) of FIG. 2). The "optical axis" is defined in consideration of the line that can be a representation of the optical path from the point of view of energy transmission of the measurement light.

As the light emitting unit 42, for example, a light guide plate can be used. The light guide plate is a plate formed by performing special processing on the surface of, for example, a resin plate or a quartz plate so that light incident from one end surface is uniformly surface-emitted from the other end surface. As a resin, for example, acrylic, polycarbonate, polystyrene, polyolefine, an ultraviolet curable resin, or a thermosetting resin can be used. In order to uniformly illuminate the subject surfaces on both sides of the transducer array 20, it is preferable that the light guide plate has, for example, a front-thick tapered shape and the width of the transducer array 20 in the array direction is substantially the same as the maximum width of the light guide plate. Therefore, it is possible to widen the propagation range of the measurement light over the array direction of the transducer array 20. The maximum width of the light guide plate in the optical axis direction is preferably 10 mm to 40 mm.

The connector unit 45a is provided at one end of the cable 40 on the opposite side of a side where the housing 11a is provided, and an incidence end portion of the bundle fiber 41 is disposed within the connector unit 45a. The connector unit 45a has a structure that is detachable and attachable from and to a mounting unit 45b of the light ultrasound system 12 as an apparatus body of the present invention. Accordingly, the probe 11 is connected to the light ultrasound system 12 when the connector unit 45a is mounted in the mounting unit 45b.

The storage unit 43 stores information relevant to the setting of the intensity of measurement light. This information is information regarding the optical structure or the optical performance of the probe 11, and is referred to when setting the light intensity of the laser light L as measurement light. The details of the specific content of the information and a method of using the information will be described later. The storage unit 43 is provided inside the connector unit 45a in the present embodiment. However, the storage unit 43 may be provided inside the housing 11a.

<Light Ultrasound System>

The light ultrasound system 12 has the receiving circuit 21, an AD conversion unit 22, a receiving memory 23, a photoacoustic image generation unit 24, a display control unit 30, a reading unit 31, a control unit 34, the laser unit 35, a variable attenuator 44a, and the mounting unit 45b. In the present embodiment, the light ultrasound system 12 corresponds to the apparatus body in the present invention, and the receiving circuit 21, the AD conversion unit 22, the receiving memory 23, the photoacoustic image generation unit 24, and the display control unit 30 correspond to a signal processing unit in the present invention as a whole.

The laser unit 35 has, for example, a solid state laser light source using a Q switch that emits laser light, and outputs the laser light L as measurement light to irradiate the subject M. For example, the laser unit 35 is configured so as to output laser light in response to a trigger signal from the control unit 34 of the light ultrasound system 12. It is preferable that the laser unit 35 outputs pulsed light having a pulse width of 1 nsec to 100 nsec as the laser light. For example, in the present embodiment, the light source of the laser unit 35 is an alexandrite laser light source using a Q switch. In addition to the alexandrite laser light source, the laser unit 35 can also be a YAG-SHG-OPO laser light source or a Ti-Sapphire laser light source capable of outputting laser light in the near-infrared wavelength range similarly.

The wavelength of laser light is appropriately determined by the light absorption characteristics of an absorber in a subject as a measurement target. For example, in a case where the measurement target is hemoglobin in the body (that is, in the case of imaging blood vessels), it is preferable, in general, that the wavelength is a wavelength belonging to the near-infrared wavelength range. The near-infrared wavelength range means a wavelength range of approximately 700 nm to 850 nm. However, it is natural that the wavelength of the laser light is not limited thereto. In addition, the laser light may have a single wavelength, or may include a plurality of wavelengths (for example, 750 nm and 800 nm). In a case where the laser light includes a plurality of wavelengths, light beams having these wavelengths may be simultaneously emitted to the subject M, or may be emitted while being switched alternately.

The control unit 34 controls each unit of the photoacoustic image generation apparatus 10, and includes a trigger control circuit (not shown) in the present embodiment. The trigger control circuit transmits a light trigger signal to the laser unit 35, for example, when the measurement is started. Then, in the laser unit 35, a flash lamp is lit to start the excitation of the laser rod. Then, the excitation state of the laser rod is maintained, and the laser unit 35 can output pulsed laser light. Thereafter, the control unit 34 transmits a Qsw trigger signal to the laser unit 35 from the trigger control circuit. Accordingly, the Q value of the resonator is switched to trigger laser oscillation. That is, the control unit 34 controls the output timing of the pulsed laser light from the laser unit 35 using the Qsw trigger signal. In the present embodiment, the control unit 34 transmits a sampling trigger signal to the AD conversion unit 22 simultaneously with the transmission of the Qsw trigger signal. The sampling trigger signal is a signal of the start timing of the sampling of the photoacoustic signal in the AD conversion unit 22. Thus, it is possible to sample the photoacoustic signal in synchronization with the output of laser light by using the sampling trigger signal.

The receiving circuit 21 receives the photoacoustic signal detected by the probe 11. The photoacoustic signal received by the receiving circuit 21 is transmitted to the AD conversion unit 22.

The AD conversion unit 22 samples the photoacoustic signal received by the receiving circuit 21, and converts the sampled photoacoustic signal into a digital signal. The AD conversion unit 22 samples a photoacoustic signal received at a predetermined sampling period, for example, based on the AD clock signal having a predetermined frequency.

The receiving memory 23 stores data (photoacoustic data) of the photoacoustic signal sampled by the AD conversion unit 22. Then, the receiving memory 23 outputs the photoacoustic data detected by the probe 11 to the photoacoustic image generation unit 24.

The photoacoustic image generation unit 24 reconstructs the data of one line by adding the pieces of photoacoustic data stored in the receiving memory 23 to each other with a delay time corresponding to the position of the ultrasound transducer, and generates data of a tomographic image (photoacoustic image) based on the photoacoustic data of each line. The photoacoustic image generation unit 24 may perform reconstruction using a circular back projection (CBP) instead of the delay addition method. The photoacoustic image generation unit 24 outputs the data of the photoacoustic image generated as described above to the display control unit 30.

The display control unit 30 displays the photoacoustic image on the display unit 14, such as a display device, based on the generated photoacoustic image data. In a case where a plurality of photoacoustic images are acquired by the probe 11 having an array of transducers arranged in a two-dimensional manner or by a probe scan, the display control unit 30 can generate volume data based on the photoacoustic images and display a three-dimensional image on the display unit 14, for example.

The mounting unit 45b is a unit in which the connector unit 45a of the probe 11 is mounted. That is, the connector unit 45a and the mounting unit 45b form a connector structure that electrically connects the probe 11 and the receiving circuit 21 to each other and optically connects the probe 11 and the laser unit 35 to each other. As such a connector, for example, a multi-core connector can be used. In this case, some of a plurality of cores may be assigned for electrical connection between the probe 11 and the receiving circuit 21, and the other cores may be assigned for optical connection between the probe 11 and the laser unit 35. In addition, a plurality of mounting units 45b may be provided. In this case, different types of probes are mounted in the respective mounting units. The probe to be actually used for measurement is selected, for example, by the operation of the user using the input unit 15.

In a case where the probe 11 is mounted in the mounting unit 45b of the light ultrasound system 12, the reading unit 31 reads "information relevant to the setting of the intensity of measurement light" stored in the storage unit 43 of the probe 11. The read information is transmitted to the control unit 34. The control unit 34 controls the driving of the variable attenuator 44a based on the information received from the reading unit 31. The reading timing is not particularly limited, and the information may be read immediately after the probe is mounted or may be read at a predetermined timing before the laser light is output. In addition, in the case of performing measurement continuously thereafter using the probe that has read the information once, the information read first can be used in the second and subsequent measurements. In a case where different types of probes 11 are mounted in the light ultrasound system 12, the reading unit 31 reads information from the storage unit of the probe selected by the user, for example.

The variable attenuator 44a corresponds to an intensity adjusting unit of the present invention, and is a unit that adjusts the intensity of the laser light L based on the information read by the reading unit 31.

Hereinafter, the specific content of the above information, a method of using the information, and a method of adjusting the intensity of the laser light L based on the information will be described.

As described above, as a probe (especially, an acoustic wave detection unit), various probes having different shapes, structures, and performance depending on the measurement conditions, such as a measurement purpose, a measurement method, and a measurement part, are prepared. Corresponding to these types, in the probes for photoacoustic measurement, the optical structure for guiding the measurement light differs depending on the type. For example, FIG. 3A is a schematic cross-sectional view showing a linear type probe, and FIG. 3B is a schematic cross-sectional view showing a convex type probe. In a linear type probe 11b, as a light emitting unit, a light guide plate 42a having a linear light emitting surface is disposed corresponding to a transducer array 20a configured to include ultrasound transducers that are arranged in a straight line. The spread angle of the laser light L emitted through the light guide plate 42a is $\varphi 1$. On the other hand, in a convex type probe 11c, as a light emitting unit, a light guide plate 42b having an arc-shaped light emitting surface is disposed corresponding to a transducer array 20b configured to include ultrasound transducers that are arranged in an arc shape. The spread angle of the laser light L emitted through the light guide plate 42b is $\varphi 2$ ($>\varphi 1$). Thus, if the types of probes are different, even if the light density of the laser light L incident on each probe is equal, the light density when the laser light L is emitted to the subject is not necessarily equal due to the difference in the optical structure. Therefore, the light density changes depending on a probe to be used.

Therefore, in the present invention, each probe has "information relevant to the setting of the light intensity of the laser light L (measurement light)" in advance, and the light intensity of the laser light L is adjusted before the laser light L is incident on the probe 11, so that the light intensity of the laser light L when the laser light L is incident on the probe 11 (hereinafter, simply referred to as "at the time of incidence") is within an appropriate range in the measurement using a probe having the information, based on the information. That is, the probe 11 of the present invention holds information that is useful for the setting of the light intensity at the time of incidence of the laser light L. Therefore, if the light intensity of the laser light L is set based on the information that the probe 11 holds, it is possible to perform measurement inevitably with the light intensity suitable for the probe 11. A specific value of the light intensity suitable for measurement of the probe can be appropriately determined, for example, from the point of view that a high-quality image can be obtained or the light density does not exceed the MPE or both. In addition, "before the laser light is incident on the probe" means a stage before the time when the laser light is incident on the probe, and is a meaning including not only an arbitrary stage until laser light is incident on the probe after the laser light is emitted from a light source but also the time at which laser light is emitted from the light source.

The information relevant to the setting of the light intensity of the laser light L (measurement light) includes identification information for identifying the type of the probe, for example. This is because the optical structure in the probe is determined to some extent if the type of the probe can be identified and accordingly the relationship between the light density when the laser light is incident on the probe and the light density when the laser light is emitted from the probe (hereinafter, simply referred to as "at the time of emission"), that is, the degree of change in the light density at the time of emission with respect to the light density at the time of incidence, can be estimated. If the relationship can be estimated, it is possible to set the light intensity of the laser light at the time of incidence, based on the relationship, so that a desired light density is obtained at the time of emission of laser light. The type of the probe is a classification based on the characteristics of the probe or its component (for example, size and applications of the probe, structure and size of the acoustic wave detection unit, and specific configuration and material of the optical structure). For the identification information, the format of the information is not particularly limited as long as it is possible to identify or specify the optical structure in the probe. For example, the identification information is code data given for each type of probe, which includes a string of characters and symbols.

Type information for identifying the type of the probe is included in the above identification information. In particular, it is preferable that the type information is for identifying that the type of the probe is any one of a linear type, a convex type, and a sector type. These types are classifications based on the structure of the transducer array (acoustic wave detection unit). Accordingly, since differences in these types are closely related to differences in the optical structure (for example, refer to FIGS. 3A and 3B), such type information is useful when estimating the relationship between the light density of the laser light at the time of incidence and the light density of the laser light at the time of emission.

In addition, it is preferable that the identification information includes emission area information indicating the area of the light emitting surface of the probe. The light emitting surface of the probe is a surface of a probe portion, through which the laser light has passed finally, before the laser light is emitted to the subject. Accordingly, the light emitting surface of the probe is usually a light emitting surface of a light emitting portion. Or, in a case where the light emitting portion is included in the probe housing, the light emitting surface of the probe is a surface of the optical window provided in the housing. In addition, in a case where an attachment, such as an acoustic lens, is attached to the probe, the light emitting surface of the probe is a surface of the attachment through which laser light passes. If the area of the light emitting surface (or the size of the probe) is different even if the type of the probe is the same, the relationship between the light density of the laser light at the time of incidence and the light density of the laser light at the time of emission changes. Therefore, such emission area information is also useful in estimating the relationship between the light density of the laser light at the time of incidence and the light density of the laser light at the time of emission. Although the emission area information is independent of the identification information in the above explanation, the present invention is not limited thereto. That is, if even the size of the probe can be identified based on the identification information, it is possible to include the emission area information in the identification information.

In addition, the information relevant to the setting of the light intensity of the laser light L may include optical performance information indicating the optical performance of the probe, for example. How the probe guides laser light is closely related to the light density at the time of emission of the laser light. Accordingly, if such optical performance is known, it is possible to set the light intensity at the time of incidence of the laser light in consideration of the optical performance. In addition, the information relevant to the setting of the light intensity of the laser light L may include only the identification information or only the optical performance information, or may include the identification information and the optical performance information at the same time. Even in a case where the information relevant to the setting of the light intensity of the laser light L includes the identification information and the optical performance information at the same time, using either one of the identification information and the optical performance information is sufficient. For example, either one of the identification information and the optical performance information is used by default.

The optical performance information is, for example, light density information indicating the degree of change (for example, the amount of change or the rate of change) in the light density (for example, a maximum value on the emission surface) at the time of emission of laser light with respect to the light density (for example, a maximum value within the incidence surface) at the time of incidence of laser light. Since such light density information is the relationship itself between the light density at the time of incidence of the laser light and the light density at the time of emission of the laser light, the light density information is useful when setting the light intensity at the time of incidence of the laser light.

The optical performance information may include transmittance information indicating the transmittance of laser light in the probe or light intensity profile information indicating the light intensity profile when measurement light is emitted from the probe. If it is known how much laser light is transmitted as a whole and/or which kind of light intensity profile is formed by the emitted laser light, it is possible to set the light intensity of the laser light in consideration of the information. In addition, the optical performance information may include information indicating the energy loss of laser light in the probe.

Setting of the light intensity of the laser light based on the above information is performed using a look-up table generated in advance, for example. For example, a look-up table is generated by the following procedure. First, the optical performance of the probe, such as a light intensity profile, a transmittance, and the amount of energy loss, on the light emitting surface (for example, reference numeral S1 in the case of the probe 11b or reference numeral S2 in the case of the probe 11c; refer to FIGS. 3A and 3B) is measured. Then, the light intensity of laser light, at which the amount of light is the MPE, on the light emitting surface of the probe is calculated. Then, a system margin (for example, 90% of MPE) is set, and the default light intensity of the probe is calculated. That is, in a case where the default laser light is incident on the probe, the light density on the light emitting surface of the probe has a value having the above system margin with respect to the MPE. Such measurement is performed for a plurality of different types of probes. Then, these results are summarized in a table in which the type of the probe (optical structure) or the optical performance of the probe is associated with the default light intensity of the probe. The table data is stored, for example, in a memory (not shown) in the photoacoustic image generation apparatus 10. In addition, such table data may be stored in a storage device outside the photoacoustic image generation apparatus 10 (for example, an external hard disk drive attached to the apparatus or a storage region on a network), so that the photoacoustic image generation apparatus 10 acquires the table data when necessary.

In the present embodiment, for example, the control unit 34 has a look-up table, and the control unit 34 checks the information received from the reading unit 31 with reference to the look-up table. By using the look-up table described above, the control unit 34 can associate the type of the probe or the optical performance of the probe with the default light intensity.

Alternatively, setting of the light intensity of the laser light based on the above information is performed using a standard function (calibration curve) generated in advance, for example. For example, a standard function is generated by the following procedure. In the same manner as described above, a default light intensity is calculated for each of a plurality of different types of probes. Then, based on these results, a standard function showing the relationship between the parameter value relevant to the optical performance of the probe and the default light intensity is calculated. The standard function is stored, for example, in a memory (not shown) in the photoacoustic image generation apparatus 10. It is not possible to directly associate the type of the probe with the default light intensity using the standard function. However, for example, by generating a table for converting the type of the probe into the parameter value relevant to the optical performance reflecting the type, it is possible to indirectly associate the type of the probe with the default light intensity using the standard function.

In addition, although the type of the probe or the optical performance of the probe is associated with the default light intensity of the probe in the above explanation, the present invention is not limited thereto. For example, the type of the probe or the optical performance of the probe may be associated with a light intensity adjusting method for realizing the default light intensity. Specifically, in a case where the default light intensity of a certain probe is realized by inserting an attenuator, such as an ND filter, on the optical path of laser light, it is possible to associate the type of the probe or the optical performance of the probe with the adjustment method of "insertion of an attenuator". Alternatively, in a case where the default light intensity of a certain probe is realized by making a variable attenuator attenuate the light intensity of laser light to a certain fixed degree, it is possible to associate the type of the probe or the optical performance of the probe with the degree of attenuation. Thus, the information relevant to the setting of the light intensity of laser light can be associated with the target value itself of the setting of the light intensity of the laser light or "adjustment conditions", such as an adjustment method for realizing the target value.

Next, a method of adjusting the intensity of the laser light L based on the above information will be described. In the present embodiment, the light intensity of the laser light L is adjusted using a variable attenuator. FIGS. 4A to 4C are schematic diagram showing an example of the variable attenuator. The variable attenuator 44a according to the present embodiment is configured to include, for example, a $\lambda/2$ plate 46 and a polarizing beam splitter 47, and is a polarization variable attenuator that adjusts the amount of light using the polarization of the laser light. A rotation mechanism is provided in the λ/2 plate 46, so that the λ/2 plate 46 can rotate around the optical axis. In a case where the light intensity of the laser light L is not attenuated, the λ/2 plate 46 is maintained at an angle at which only a p-polarized light component Lp is incident on the splitter surface of the polarizing beam splitter 47, and the p-polarized light component Lp (that is, all laser beams) passes through the splitter surface (refer to FIG. 4A). When the λ/2 plate 46 rotates around the optical axis from the state shown in FIG. 4A, the polarization direction of the laser light L also rotates. Then, an s-polarized light component Ls of the laser light L with respect to the splitter surface is generated. The s-polarized light component Ls is reflected on the splitter surface, and only the remaining p-polarized light component Lp passes through the splitter surface (refer to FIG. 4B). In addition, when the λ/2 plate 46 rotates around the optical axis from the state shown in FIG. 4B, the s-polarized light component Ls of the laser light L with respect to the splitter surface is increased, and the p-polarized light component Lp passing through the splitter surface is reduced (refer to FIG. 4C). Thus, in the polarization variable attenuator, it is possible to adjust the light intensity of the laser light L according to the rotation angle of the λ/2 plate. Thereafter, the laser light L whose light intensity has been adjusted is incident on the bundle fiber 41 using an optical system (not shown), such as a condensing lens, for example.

Hereinafter, steps of photoacoustic measurement according to the present embodiment will be described. First, a user of the photoacoustic image generation apparatus 10 mounts the connector unit 45*a* of the probe 11 in the mounting unit 45*b* of the light ultrasound system 12. At this time, the reading unit 31 reads information relevant to the setting of the intensity of measurement light from the storage unit 43 of the probe 11, and transmits the read information to the control unit 34. The control unit 34 checks the received information and data on the relevant look-up table with reference to the look-up table generated in advance, and acquires adjustment conditions associated with the information. In a case where the adjustment conditions associated with the information are not present, for example, the measurement is ended at that time, and a notification indicating that the measurement has been ended is displayed on the display unit 14. In a case where the adjustment conditions associated with the read information can be acquired, the control unit 34 controls the variable attenuator 44*a* to adjust the light intensity of the laser light L according to the adjustment conditions. For example, in a case where the set target value of the light intensity of laser light is designated in the adjustment conditions, the control unit 34 changes the rotation angle of the λ/2 plate 46 of the variable attenuator 44*a* to a rotation angle at which the light intensity becomes the target value. Alternatively, in a case where the rotation angle of the λ/2 plate 46 for realizing the target value is designated in the adjustment conditions, the control unit 34 adjusts the rotation angle of the λ/2 plate 46 to the designated angle. Thus, preparation for adjusting the light intensity of the laser light L is completed.

The user holds the probe 11, and brings the tip into contact with the subject. Then, the laser light L is emitted from the light emitting unit 42, so that the subject is irradiated with the laser light L. Then, photoacoustic waves generated due to the irradiation of the laser light are detected by the probe 11, and a photoacoustic image is generated based on the signal. Then, the photoacoustic image is transmitted to the display control unit 30, so that the photoacoustic image is displayed on the display unit 14. In the case of continuing the measurement, the above steps are repeated. Otherwise, the above steps are ended. However, in the case of repeating the measurement using the same probe 11, it is not necessary to read the information again since the adjustment of the light intensity of the laser light L has already ended.

As described above, in the photoacoustic measurement apparatus and the probe for photoacoustic measurement according to the present embodiment, the probe has the information relevant to the setting of the intensity of measurement light in advance, and the light intensity of the laser light when the laser light is incident on the probe is adjusted so as to be within an appropriate range for measurement using a probe having the information based on the information. Therefore, in the photoacoustic measurement apparatus and the probe for photoacoustic measurement according to the present embodiment, the light intensity of the laser light can be set to be within the appropriate range for measurement using the probe even without actual measurement. In the invention disclosed in JP2011-229735A, the light density distribution of light emitted to the body is measured, and the amount of light is adjusted such that the maximum value does not exceed the maximum permissible exposure. In the present invention, however, the measurement of the amount of light density described above is not necessary. As a result, by the photoacoustic measurement apparatus and the probe for photoacoustic measurement according to the present embodiment, it is possible to easily set the light density of measurement light in the case of using a probe for photoacoustic measurement that is detachable and attachable from and to the apparatus body.

In addition, in the case of handling a plurality of probes (for example, handheld type probes) that are detachable and attachable from and to the apparatus body, it is possible to set the light intensity of laser light just by attaching a probe to be used to the apparatus body or just by selecting a probe to be used.

Although the case where the variable attenuator 44*a* is a polarization variable attenuator has been described in the present embodiment, the present invention is not limited thereto. For example, FIGS. 5A and 5B are schematic diagrams showing another example of the variable attenuator. A variable attenuator 44*b* shown in FIGS. 5A and 5B is a transmission variable attenuator configured to include a step variable ND (dimming) filter 48 having a plurality of regions where optical densities are different and a driving unit 49 for driving the ND filter 48 so as to rotate. The ND filter 48 has three regions 50*a*, 50*b*, and 50*c* having different optical densities. For example, the optical density of the region 50*a* is the lowest, and the optical density of the region 50*c* is the highest. The ND filter 48 is disposed on the optical path of the laser light L, and the driving unit 49 rotates a rotary shaft 48*a* to perform switching between the regions disposed on the optical path. That is, the light intensity of the laser light L is adjusted according to which of the regions 50*a*, 50*b*, and 50*c* is disposed on the optical path. For example, the control unit 34 gives an instruction to the driving unit 49 so that a region having a predetermined optical density is disposed on the optical path based on the information received from the reading unit 31. Then, preparation for adjustment of the light intensity of the laser light L is completed by arranging a region having a predetermined optical density on the optical path. Thereafter, the laser light L whose light intensity has been adjusted is incident on the bundle fiber 41 using an optical system (not shown), such as a condensing lens, for example.

Instead of the step variable ND filter 48, a continuous variable ND filter can also be used. In FIGS. 5A and 5B, in order to prevent damage to the bundle fiber 41 and surrounding members (ferrule or the like), a cap member 40a is provided at the incidence end of the bundle fiber 41. As the cap member 40a, for example, a quartz rod having high light energy resistance can be used.

In addition, the information relevant to the setting of the intensity of measurement light may be attenuation necessity information indicating whether or not it is necessary to attenuate the light intensity of the laser light. In this case, an ND filter having a certain optical density is used as an intensity adjusting unit instead of the variable attenuator described above, and the light intensity is adjusted according to the adjustment conditions, such as insertion or non-insertion of the ND filter.

In addition, although the case where the laser unit 35 and the variable attenuator 44a are disposed in the light ultrasound system 12 has been described in the present embodiment, the present invention is not limited thereto. That is, the laser unit 35 and the variable attenuator 44a may be disposed outside the light ultrasound system 12. In this case, the connector unit 45a can be made to have a bifurcated structure of a connector for electrical connection and a connector for optical connection.

Second Embodiment

Next, a photoacoustic measurement apparatus according to a second embodiment will be described. In the present embodiment, the photoacoustic measurement apparatus is the photoacoustic image generation apparatus 10 as in the first embodiment. The photoacoustic image generation apparatus 10 according to the present embodiment is different from the first embodiment in that a beam diameter converter 44c is provided instead of the variable attenuator 44a. Accordingly, the detailed explanation of the same configuration as in the first embodiment will be omitted unless otherwise required.

FIG. 6 is a block diagram schematically showing the configuration of a photoacoustic image generation apparatus (photoacoustic measurement apparatus) according to the present embodiment. As shown in FIG. 6, the photoacoustic image generation apparatus 10 according to the present embodiment includes a probe 11, a light ultrasound system 12, a display unit 14, and an input unit 15. In addition, the light ultrasound system 12 has a receiving circuit 21, an AD conversion unit 22, a receiving memory 23, a photoacoustic image generation unit 24, a display control unit 30, a reading unit 31, a control unit 34, a laser unit 35, the beam diameter converter 44c, and a mounting unit 45b.

The beam diameter converter 44c corresponds to an intensity adjusting unit of the present invention, and is a unit that adjusts the intensity of the laser light L based on the "information relevant to the setting of the light intensity of the laser light L" read by the reading unit 31.

That is, in the present embodiment, the light intensity of the laser light L is adjusted using the beam diameter converter 44c. FIGS. 7A and 7B are schematic diagrams showing an example of the beam diameter converter. The beam diameter converter 44c according to the present embodiment is configured to include a beam expander 51 for enlarging or reducing the beam diameter, for example. For example, in certain adjustment conditions, the beam expander 51 controls the beam diameter such that the beam diameter of laser light La is equal to the diameter of the bundle fiber 41 (refer to FIG. 7A). By making the beam diameter of the laser light L equal to the diameter of the bundle fiber 41, it is possible to avoid energy concentration on the incidence surface. Therefore, it is possible to prevent damage to the bundle fiber 41. In addition, in order to prevent damage to the bundle fiber 41 more reliably, also in the bundle fiber 41 according to the present embodiment, a cap member 40a is provided at the incidence end. On the other hand, in the case of reducing the light density at the time of emission from the state shown in FIG. 7A, the beam expander 51 controls the beam diameter such that the beam diameter of laser light Lb is larger than the diameter of the bundle fiber 41 (refer to FIG. 7B). Then, the laser light incident on the bundle fiber 41 is reduced, and the light density at the time of emission of the laser light L is reduced. In this case, in order to prevent damage to the surrounding members of the bundle fiber 41 by laser light that is not incident on the bundle fiber 41, it is preferable to provide, for example, a ring member 40b as shown in FIGS. 7A and 7B. In FIG. 7, the ring member 40b is fitted into a cap member in order to receive the laser light that is not incident on the bundle fiber 41. The ring member 40b is formed of a high light energy resistant material, such as sapphire that is excellent in light absorption in the wavelength band of laser light to be used, for example. In addition, the light intensity of the laser light L may also be adjusted using a beam diameter converter after attenuating the intensity of measurement light using a variable attenuator.

As described above, in the photoacoustic measurement apparatus and the probe for photoacoustic measurement according to the present embodiment, the probe has the information relevant to the setting of the intensity of measurement light in advance, and the light intensity of the laser light when the laser light is incident on the probe is adjusted so as to be within an appropriate range for measurement using a probe having the information based on the information. Therefore, the same effect as in the first embodiment is obtained.

Third Embodiment

Next, a photoacoustic measurement apparatus according to a third embodiment will be described. In the present embodiment, the photoacoustic measurement apparatus is the photoacoustic image generation apparatus 10 as in the first embodiment. The photoacoustic image generation apparatus 10 according to the present embodiment is different from the first embodiment in that the light intensity itself of the laser light L emitted from the laser unit 35 is adjusted without the variable attenuator 44a being provided. Accordingly, the detailed explanation of the same configuration as in the first embodiment will be omitted unless otherwise required.

FIG. 8 is a block diagram schematically showing the configuration of a photoacoustic image generation apparatus (photoacoustic measurement apparatus) according to the present embodiment. As shown in FIG. 8, the photoacoustic image generation apparatus 10 according to the present embodiment includes a probe 11, a light ultrasound system 12, a display unit 14, and an input unit 15. The light ultrasound system 12 has a receiving circuit 21, an AD conversion unit 22, a receiving memory 23, a photoacoustic image generation unit 24, a display control unit 30, a reading unit 31, a control unit 34, a laser unit 35, and a mounting unit 45b.

In the present embodiment, the laser unit 35 itself functions as an intensity adjusting unit, so that the light intensity of the laser light L when the laser light L is emitted from the laser unit 35 is adjusted. The laser unit 35 has a solid state laser light source using a Q switch that emits laser light, for example. In the laser unit 35, when a light trigger signal is received from the trigger control circuit of the control unit 34, a flash lamp is lit to start the excitation of the laser rod. Then, the excitation state of the laser rod is maintained, and the laser unit 35 can output pulsed laser light. Thereafter, the control unit 34 transmits a Qsw trigger signal to the laser unit 35 from the trigger control circuit. As a result, laser oscillation occurs.

Here, the light intensity of the laser light increases or decreases depending on the laser oscillation conditions. For example, if the number of flash lamps to excite the laser rod or the charge voltage of each flash lamp is increased, the laser rod is excited to a higher state, and the light intensity of the laser light L is also increased. In addition, it is also possible to control the light intensity of the laser light L, for example, by increasing or decreasing the delay time until the Qsw trigger signal is output after a light trigger signal is output.

Therefore, based on the information received from the reading unit 31, the control unit 34 gives an instruction to the laser unit 35, so that the light intensity of the laser light becomes a desired value by oscillating the laser light under the laser light oscillation conditions corresponding to the information, with reference to the look-up table in which the type of the probe or the optical performance of the probe and the laser light oscillation conditions are associated with each other. Thereafter, the laser light L whose light intensity has been adjusted by the laser unit 35 is incident on the bundle fiber 41 using an optical system (not shown), such as a condensing lens, for example.

As described above, in the photoacoustic measurement apparatus and the probe for photoacoustic measurement according to the present embodiment, the probe has the information relevant to the setting of the intensity of measurement light in advance, and the light intensity of the laser light when the laser light is incident on the probe is adjusted so as to be within an appropriate range for measurement using a probe having the information based on the information. Therefore, the same effect as in the first embodiment is obtained.

Fourth Embodiment

Next, a photoacoustic measurement apparatus according to a fourth embodiment will be described. In the present embodiment, the photoacoustic measurement apparatus is the photoacoustic image generation apparatus 10 as in the first embodiment. The present invention is different from the first embodiment in that not only the photoacoustic image but also an ultrasound image is generated. Accordingly, the detailed explanation of the same components as in the first embodiment will be omitted unless otherwise required.

The photoacoustic image generation apparatus 10 of the present embodiment includes a probe 11, a light ultrasound system 12, a display unit 14, and an input unit 15.

<Light Ultrasound System>

The light ultrasound system 12 of the present embodiment includes an ultrasound image generation unit 29 and a transmission control circuit 33 in addition to the configuration of the photoacoustic image generation apparatus shown in FIG. 1. In the present embodiment, the receiving circuit 21, the AD conversion unit 22, the receiving memory 23, the photoacoustic image generation unit 24, the ultrasound image generation unit 29, and the display control unit 30 correspond to a signal processing unit in the present invention as a whole.

In the present embodiment, the probe 11 performs output (transmission) of the ultrasound wave to the subject and detection (reception) of the reflected ultrasound wave (reflected acoustic wave) from the subject of the transmitted ultrasound wave in addition to the detection of the photoacoustic signal. As an ultrasound transducer for transmitting and receiving ultrasound waves, the transducer array 20 in the present invention may be used, or a new ultrasound transducer that is separately provided in the probe 11 for the transmission and reception of ultrasound waves may be used. In addition, transmission and reception of ultrasound waves may be separated. For example, ultrasound waves may be transmitted from a position different from the probe 11, and reflected ultrasound waves of the transmitted ultrasound waves may be received by the probe 11.

When generating an ultrasound image, the control unit 34 transmits an ultrasound wave transmission trigger signal for instructing the transmission control circuit 33 to perform ultrasound wave transmission. When the trigger signal is received, the transmission control circuit 33 makes the probe 11 transmit ultrasound waves. The probe 11 detects reflected ultrasound waves from the subject after the transmission of ultrasound waves.

The reflected ultrasound waves detected by the probe 11 are input to the AD conversion unit 22 through the receiving circuit 21. The control unit 34 transmits a sampling trigger signal to the AD conversion unit 22 according to the timing of ultrasound wave transmission, thereby starting the sampling of reflected ultrasound waves. The AD conversion unit 22 stores the sampling signal of the reflected ultrasound waves in the receiving memory 23. Either the sampling of the photoacoustic signal or the sampling of the reflected ultrasound wave may be performed first.

The ultrasound image generation unit 29 generates the data of the ultrasound image by performing signal processing, such as reconstruction processing, detection processing, and logarithmic conversion processing, based on the reflected ultrasound wave (sampling signal) detected by the transducer array 20 of the probe 11. In the generation of the image data, it is possible to use a delay summation method or the like as in the generation of image data in the photoacoustic image generation unit 24. The ultrasound image generation unit 29 outputs the data of the ultrasound image generated as described above to the display control unit 30.

For example, the display control unit 30 displays the photoacoustic image and the ultrasound image separately on the display unit 14, or displays a composite image of the photoacoustic image and the ultrasound image on the display unit 14. The display control unit 30 performs image combination by superimposing the photoacoustic image and the ultrasound image, for example.

In the present embodiment, the photoacoustic measurement apparatus generates an ultrasound image in addition to the photoacoustic image. Therefore, in addition to the effect of the first embodiment, it is possible to observe a portion, which cannot be imaged in the photoacoustic image, by referring to the ultrasound image.

What is claimed is:

1. A photoacoustic measurement apparatus, comprising:
   an apparatus body having a signal processor including circuitry that is configured to perform signal processing on a photoacoustic wave;
   a probe that is configured to be detachable and attachable from and to the apparatus body and that is configured to emit measurement light incident on the probe toward a subject; and
   a controller that is configured to adjust an intensity of the measurement light, wherein the probe has a light guide unit including optical fiber that is configured to guide the measurement light, an acoustic wave detection unit including a transducer array that is configured to detect the photoacoustic wave generated within the subject according to emission of the measurement light from the light guide unit, and a storage unit that stores light intensity profile information that represents the light intensity profile of the measurement light emitted by the probe, and transmits from the acoustic wave detection unit a signal of the photoacoustic wave detected by the acoustic wave detection unit to the signal processor in a state in which the probe is mounted in the apparatus body, the apparatus body has a reader that is configured to read the light intensity profile information from the storage unit, and the controller is configured to adjust the intensity of the measurement light before the measurement light is incident on the probe employing the light intensity profile information read by the reader, the light intensity profile information being information that corresponds to a type of the probe with respect to the transducer array that has different adjustment conditions of a light intensity of the measurement light when the measurement light is emitted toward the subject, due to the difference in light guide unit shape corresponding to a shape of the transducer array;

wherein the controller is configured to acquire adjustment conditions, which are associated with the light intensity profile information by a look-up table, with reference to the look-up table, and adjusts the intensity of the measurement light according to the adjustment conditions.

2. The photoacoustic measurement apparatus according to claim 1, wherein the controller is configured to adjust the light intensity by setting a calculated value, which is calculated based on the light intensity profile information, to a target value of the intensity of the measurement light.

3. The photoacoustic measurement apparatus according to claim 1, wherein the controller is configured to increase or decrease an amount of attenuation of the intensity of the measurement light using a variable attenuator.

4. The photoacoustic measurement apparatus according to claim 3, wherein the variable attenuator is a polarization variable attenuator.

5. The photoacoustic measurement apparatus according to claim 1, wherein the controller is configured to increase or decrease a beam diameter of the measurement light when the measurement light is incident on the light guide unit.

6. The photoacoustic measurement apparatus according to claim 1, wherein, in a case where there is a plurality of probes mounted in the apparatus body, the reader is configured to read the light intensity profile information from the storage unit of the probe designated by a user.

7. The photoacoustic measurement apparatus according to claim 1, wherein the probe is a handheld type probe.

8. The photoacoustic measurement apparatus according to claim 1, wherein the type of the probe with respect to the transducer array is any one of a linear type, a convex type, and a sector type.

9. A probe that is detachable and attachable from and to an apparatus body having a signal processor including circuitry for performing signal processing on a photoacoustic wave and that emits measurement light toward a subject, comprising:

a light guide unit including optical fiber that is configured to guide the measurement light;

an acoustic wave detection unit including a transducer array that is configured to detect the photoacoustic wave generated within the subject according to emission of the measurement light from the light guide unit; and a storage unit that stores light intensity profile information that represents the light intensity profile of the measurement light emitted by the probe, wherein a signal of the photoacoustic wave detected by the acoustic wave detection unit is transmitted from the acoustic wave detection unit to the signal processor in a state in which the probe is mounted in the apparatus body, the light intensity profile information being information that corresponds to a type of the probe with respect to the transducer array that has different adjustment conditions of a light intensity of the measurement light when the measurement light is emitted toward the subject, due to the difference in light guide unit shape corresponding to a shape of the transducer array.

* * * * *